United States Patent [19]
Fallon et al.

[11] Patent Number: 5,175,253
[45] Date of Patent: Dec. 29, 1992

[54] BINDING PEPTIDES

[75] Inventors: Robert J. Fallon, Chesterfield; Joseph W. Bulock, St. Peters; Steven P. Adams, St. Charles; David H. Perlmutter, Clayton, all of Mo.

[73] Assignee: Washington University, St. Louis, Mo.

[21] Appl. No.: 690,284

[22] Filed: Apr. 24, 1991

[51] Int. Cl.$^5$ .................... C07K 7/06; A61K 37/00
[52] U.S. Cl. ................................. 530/330; 514/17
[58] Field of Search .................. 530/330; 514/17

[56] References Cited

PUBLICATIONS

Travis & Salvesen, Am. Rev. Biochem. 52, 655–709 (1983).
Huber & Carrell, Biochemistry 28, 8951–8971 (1990).
Perlmutter & Pierce, Amer. J. Physiol. 257, L147–L162 (1989).
Perlmutter et al., J. Clin. Invest. 81, 1774–1780 (1988).
Perlmutter & Punsal, J. Biol. Chem. 263, 16499–16503 (1988).
Perlmutter et al., Proc. Natl. Acad. Sci. USA 87, 3753–3757 (1990).
Perlmutter et al., J. Biol. Chem. 265, 16713–16716 (1990).
Hershey & Krause, Science 247, 958–962 (1970).
Yankner et al., Science 250, 279–282 (1990).
Oltersdorf et al., Nature 341, 144–147 (1989).
Van Nostrand et al., Nature 341, 546–549 (1989).

Primary Examiner—Merrell C. Cashion, Jr.
Assistant Examiner—P. L. Touzeau
Attorney, Agent, or Firm—Scott J. Meyer

[57] ABSTRACT

Novel short peptides of up to about 20 amino acid residues are disclosed that bind to the SEC receptor. These novel peptides preferably are pentapeptides which are synthetic analogs of a pentapeptide domain in the carboxy-terminal fragment of $\alpha_1$-antitrypsin (amino acids 370–374, Phe-Val-Phe-Leu-Met [SEQ ID NO:2]). A preferred binding peptide is Phe-Val-Ala-Leu-Met [SEQ ID NO;6].

6 Claims, 10 Drawing Sheets

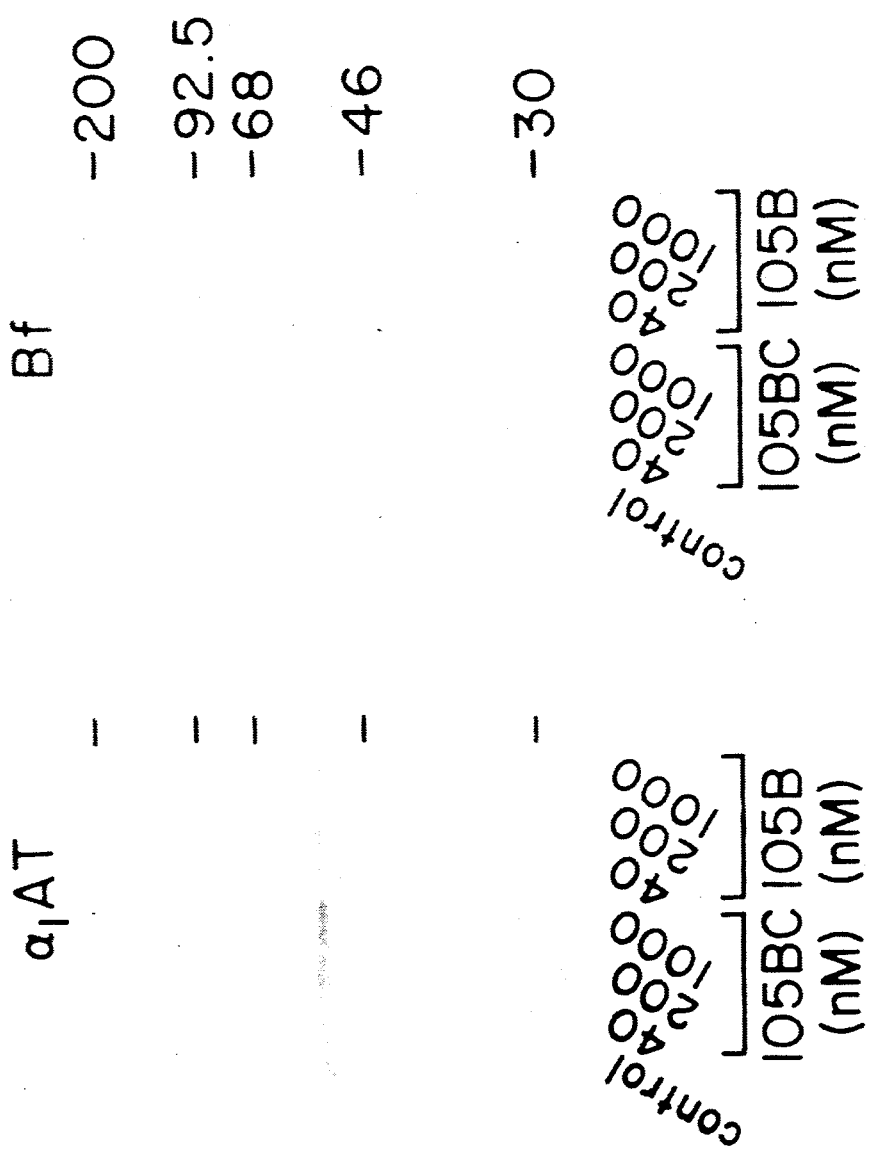

|  | 370 | | | 374 |
|---|---|---|---|---|---|
| α₁AT | F V F L M |
| AT III | F L V F I |
| α₁ACT | F L M I I |
| C1 Inh | F L F V L |
| HC II | F L F L I |
| PAI I | F L F V V |
| PAI II | F L F L I |
| α₂AP | F L F F I |
| PC Inh | F L M F I |
| PN I | F L F F I |
| TBG | F M L L I |
| CBG | F I I M I |
| Ovalbumin | F L F C I |
| Angiotensinogen | F L F A V |

FIG. 7

BINDING PEPTIDES

This invention was made with Government support under Grant No. HL37784 awarded by the National Institution of Health. The Government has certain rights in the invention.

BACKGROUND OF THE INVENTION

The present invention relates to novel binding peptides and, more particularly, to small peptides that bind to the serpin-enzyme complex or SEC receptor.

$\alpha_1$-antitrypsin ($\alpha_1$ AT) is a single-chain, 55 kDa serum glycoprotein having 394 amino acids with no disulfide bridges and containing 3 oligosaccharide side chains. It is one of the most well characterized members of a family of serum proteins referred to as serpins. See, e.g., Huber and Carrell, *Biochemistry* 28, 8951–8971 (1990); Perlmutter and Pierce *Amer. J. Physiol.* 257, L147–L162 (1989). Members of this family include inhibitors of coagulation (ATIII, heparin cofactor II, protein C inhibitor), fibrinolysis ($\alpha_2$ antiplasmin, plasminogen activator inhibitors I and II) and complement (Cl inhibitor). Several serpins such as $\alpha_1$ antichymotrypsin and protease nexin I play a role in connective tissue turnover Non-inhibitory homologues such as corticosteroid-binding globulin and thyroid hormone-binding globulin bind their hormone ligands by a serpin-like mechanism [Pemberton et al., *Nature* 336, 257–258 (1988)] while ovalbumin and angiotensinogen may serve as substrates for their cognate enzymes [Wright, *J. Biol. Chem.* 259, 14335–14337 (1984)]. Although these proteins bear only 25–30% homology in overall primary structure there are much higher degrees of homology in specific regions. Each serpin which has been examined has a reactive center within an exposed loop acting as a pseudo-substrate for its cognate enzyme. There is a tight complex formed by serpin and enzyme, structural rearrangement of the serpin and cleavage at the reactive site peptide bond which may be variable in extent. See, e.g., Travis and Salvesen, Ann. Rev. Biochem. 52, 655–709 (1983).

Since the major physiologic target of $\alpha_1$ AT is neutrophil elastase an enzyme capable of degrading many connective tissue matrix constituents, the serpin is thought to function as an inhibitor of connective tissue turnover This is supported by the fact that $\alpha_1$ AT deficiency is associated with premature development of pulmonary emphysema. See, e.g., Crystal, *J. Clin. Invest.* 95, 1343–1352 (1990). Elastase also degrades many serum proteins and, thus, perturbations in the elastase-$\alpha_1$ AT balance are believed to contribute to the defects in coagulation, fibrinolysis and complement activation which accompany systemic inflammatory states such as sepsis or adult respiratory distress syndrome See, e.g., Carrell, *J. Clin. Invest.* 77, 1427–1431 (1986). It has only recently been recognized that $\alpha_1$ AT has other potential functions. When in complex with neutrophil elastase, $\alpha_1$ AT possesses neutrophil chemoattractant properties [Banda et al., *J. Biol. Chem.* 263, 4481–14484 (1988); *J. Exp. Med.* 167, 1608–1615 (1988)] and mediates an increase in de novo biosynthesis of $\alpha_1$ AT itself [Perlmutter et al., *J. Clin. Invest.* 81, 1774–1780 (1988); Perlmutter and Punsal, *J. Biol. Chem.* 263, 16499–16503 (1988)]. These observations have suggested that structural rearrangement of the $\alpha_1$ AT molecule, during formation of a complex with elastase, exposes a domain that is recognized by a specific cell surface receptor, or receptors. In a recent report by Perlmutter et al., *Proc. Natl. Acad. Science* 87, 3753–3757 (1990), synthetic peptides of at least 16 amino acid residues and based on the sequence of a potentially exteriorly exposed and highly conserved region of the complex form of $\alpha_1$ AT were tested as candidate ligands (carboxy-terminal fragment, amino acids 359–374). $^{125}$I Peptide 105Y (SIPPEVKFNKP-FVYLI) bound specifically and saturably to a single class of receptors on HepG2 cells and human blood monocytes ($K_2=4.0\times10^{-8}$; $4.5\times10^5$ plasma membrane receptors per cells) and mediated an increase in synthesis of $\alpha_1$ AT. Binding of $^{125}$I peptide 105Y was blocked by $\alpha_1$ AT-elastase complexes but not by the corresponding native proteins Furthermore, unlabelled peptide 105Y blocked binding of $^{125}$I$\alpha_1$ AT-elastase complexes. These data indicated that at least part of the domain of $\alpha_1$ AT corresponding to peptide 105Y was available for receptor binding and that structural rearrangement of $\alpha_1$ AT during complex formation was a prerequisite for recognition by receptor. Binding of $^{125}$I peptide 105Y was also blocked by AT III-thrombin complexes, $\alpha_1$ ACT-cathepsin G complexes and, to a lesser extent C1 inhibitor-C1s complexes but not by the corresponding native proteins. Thus, the responsible cell surface receptor was referred to as the serpin-enzyme complex or SEC receptor. Subsequent studies have shown that the SEC receptor mediates endocytosis and lysosomal degradation of $\alpha_1$ AT-protease complexes [Perlmutter et al., J. Biol. Chem. 265, 16713–16716 (1990)].

The sequence of peptide 105Y which consists of the carboxy-terminal fragment, amino acids 359–374, of $\alpha_1$ AT, converted to the three-letter abbreviations, is designated herein and in the accompanying Diskette as SEQ ID NO:1, and numbered from 1 to 16 in accordance with 37 CFR 1.821-825.

BRIEF DESCRIPTION OF THE INVENTION

In accordance with the present invention, novel small, synthetic peptides are provided that bind to the serpin-enzyme complex or SEC receptor. These novel binding peptides are short peptides of up to about 20 amino acid residues that contain a minimal pentapeptide sequence which corresponds to a pentapeptide domain in the carboxy-terminal fragment of $\alpha_1$ AT (amino acids 370–374, Phe-Val-Phe-Leu-Met) [SEQ ID NO:2] and synthetic analogs thereof. A preferred binding pentapeptide is Phe-Val-Ala-Leu-Met [SEQ ID NO:6]. Other useful binding pentapeptides are, e.g., Ala-Val-Phe-Leu-Met [SED ID NO:4], Phe-Val-Phe-Leu-Ala [SEQ ID NO:5] and Phe-Val-Tyr-Leu-Ile [SEQ ID NO:3]. These results were unexpected in view of the fact that, by way of comparison, the closely related tetrapeptide Phe-Val-Tyr-Leu [SEQ ID NO:7] has virtually no binding activity against the SEC receptor, nor does the adjacent heptapeptide Glu-Val-Lys-Phe-Asn-Lys-Pro (amino acids 363–369) [SEQ ID NO:8] have any such binding activity. Likewise, the closely related hexapeptide Lys-Pro-Phe-Val-Phe-Leu (amino acids 368–373) [SEQ ID NO:9] has only minimal binding activity.

DETAILED DESCRIPTION OF THE INVENTION

While the specification concludes with claims particularly pointing out and distinctly claiming the subject matter regarded as forming the present invention, it is believed that the invention will be better understood from the following preferred embodiments of the invention taken in connection with the accompanying drawings in which:

FIG. 1 is a graphical representation which shows competition for binding of $^{125}$I peptide 105Y to HepG2 cells. For each test HepG2 cells were incubated for 2 hrs at 4° C. in binding buffer, $^{125}$I peptide 105Y at saturating concentrations (50 nM) and competing unlabelled synthetic peptides in the concentrations specified on the horizontal axis. The cells were then rinsed in phosphate buffered saline (PBS) containing 1 mM $CaCl_2$ and 1 mM $MgCl_2$, homogenized in 1 N NaOH, and cell-associated radioactivity was determined. Binding in the absence of competitor was arbitrarily designated 100% binding on the vertical axis. Each data point and set of error bars represent mean and 1 standard deviation for four separate determinations. Partial amino acid sequences of $\alpha_1$ AT and synthetic peptides are shown at the top of each of panels a, b and c.

FIG. 2 presents two bar graphs which show competition for binding and internalization of $\alpha_1$ AT$^{125}$I trypsin complexes by HepG2 cells. For panel a, HepG2 cells were incubated for 2 hours at 4° C. in binding buffer, $\alpha_1$ AT-$^{125}$I trypsin complexes in subsaturating concentrations (50 nM) and competing unlabelled proteins or synthetic peptides in 50-fold molar excess. The cells were then rinsed, homogenized and cell-associated radioactivity determined. Binding in the absence of competitor was arbitrarily designated 0% inhibition of binding on the vertical axis. Results represent mean and 1 standard deviation for 3 separate determinations of each competitor. For panel b, HepG2 cells were incubated for 1 hour at 37° C. in binding buffer, $\alpha_1$ AT$^{125}$I trypsin complexes in subsaturating concentrations (50 nM) and competing unlabelled proteins or synthetic peptides in 50-fold molar excess. The cells were then rinsed and incubated for an additional 1 hour at 4° C. in PBS containing 0.5 mg/ml Proteinase K. Radioactivity in the Proteinase K-resistant cell pellet was determined as described in the Examples hereinbelow. Internalization in the absence of competitor was arbitrarily designated 0% inhibition of internalization on the vertical axis. Results represent mean and 1 standard deviation for 3 separate determinations of each putative competitor. Partial amino acid sequences for $\alpha_1$ AT and peptides are shown at the top of each panel.

Figure 3A:
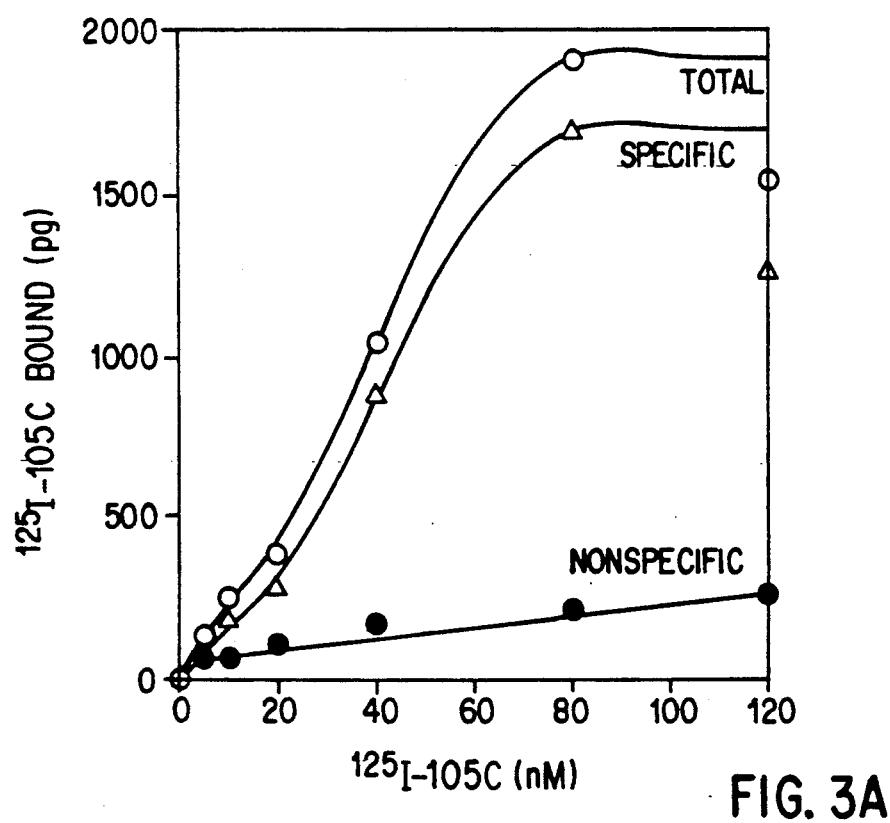
Figure 3B:
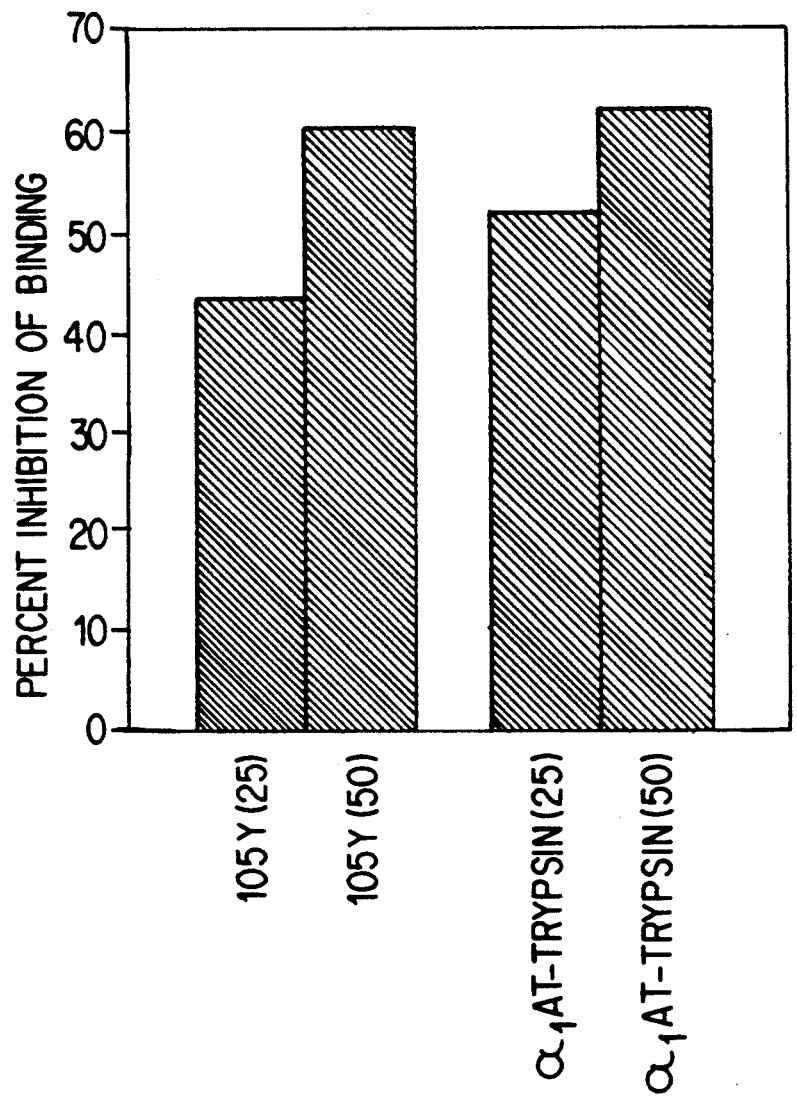

FIG. 3 is a graphical representation which shows direct binding of $^{125}$I-peptide 105C to HepG2 cells. Left panel a: cells were incubated 2 hours at 4° C. with several different concentrations of $^{125}$I peptide 105C in the absence (open circles, total ligand binding) or the presence of unlabelled peptide 105C in 200-fold molar excess (filled circles, nonspecific binding). The difference was designated specific binding (open triangles). The cells were then rinsed and cell-associated radioactivity was determined by gamma counting of cell homogenates. Right panel b: cells were incubated for 2 hours at 4° C. with $^{125}$I peptide 105C in subsaturating concentrations (50 nM) in the absence or presence of unlabelled competing proteins or peptides as indicated on the horizontal axis. The molar excess in fold of each competitor is indicated in parentheses. Binding in the absence of competitor was arbitrarily designated 0% inhibition of binding on the vertical axis.

FIG. 4 shows the effect of synthetic peptides on synthesis of $\alpha_1$ AT in human monocytes. Cells were incubated for 5 hours at 37° C. in binding buffer supplemented with polymyxin B alone (15 μg/ml) or supplemented with polymyxin B and peptide 105BC or peptide B in the specified concentrations. Cells were subjected to metabolic labelling with $^{35}$S methionine for 30 mins. and the resulting radiolabelled cell lysates subjected to analysis by immunoprecipitation followed by SDS-PAGE and fluorography. Each sample was immunoprecipitated with antihuman $\alpha_1$ AT IgG (left panel a) and then antihuman complement protein factor B (right panel b). Molecular mass markers are indicated at the right margin.

Figure 5:
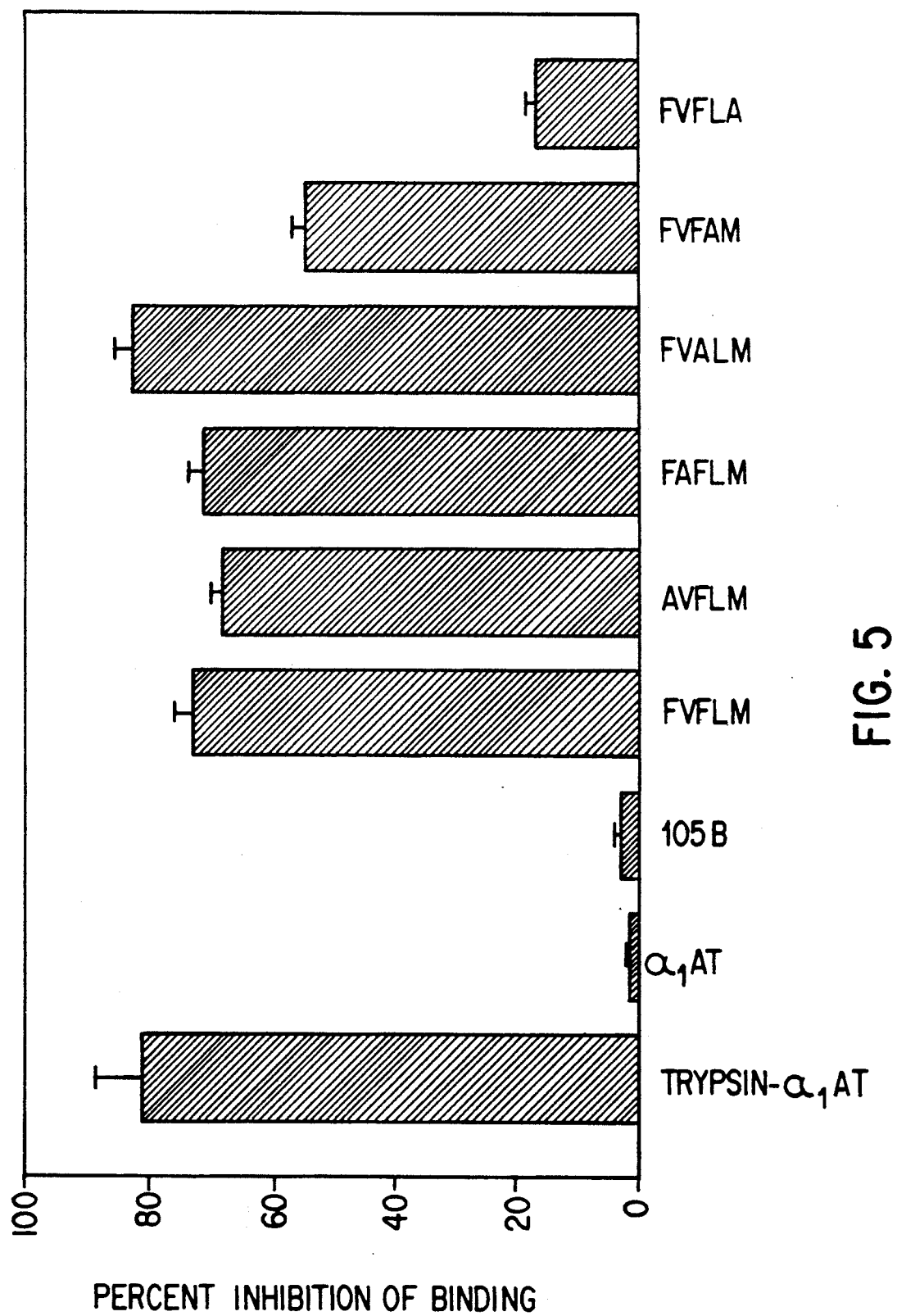

FIG. 5 is a bar graph which shows competition for binding of $^{125}$I trypsin-$\alpha_1$ AT complexes by mutant peptides. HepG2 cells were incubated for 2 hrs at 4° C. in binding buffer containing $^{125}$I trypsin-$\alpha_1$ AT complexes at subsaturating concentrations (50 nm) and putative competing unlabelled proteins or synthetic peptides in 50-fold molar excess. Each bar represents mean and 1 standard deviation for 3 separate determinations of each putative competitor.

Figure 6:
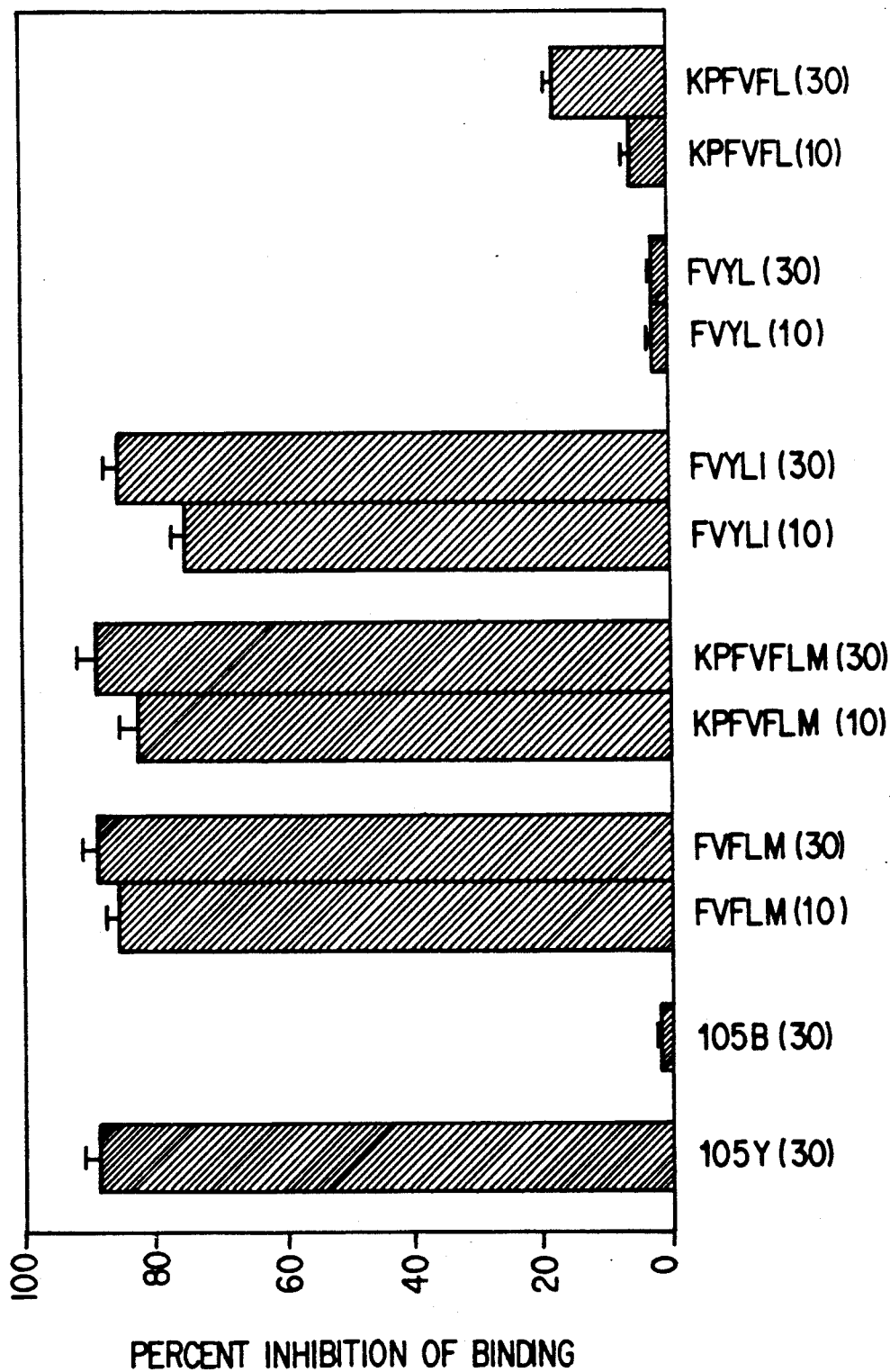

FIG. 6 is a bar graph which shows competition for binding of $^{125}$I peptide 105Y by unlabelled peptides to determine the contribution of KP 368-369 HepG2 cells were incubated for 2 hrs at 4 C in binding buffer, $^{125}$I peptide 105Y at subsaturating concentrations (50nM) and competing synthetic peptides The fold molar excess is shown in parentheses. Each bar represents mean and 1 standard deviation for 3 separate determinations.

FIG. 7 shows the sequences of serpins in regions corresponding to $\alpha_1$ AT 370-374.

The novel binding peptides of this invention can be prepared by known solution and solid phase peptide synthesis methods.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group (BOC), various coupling reagents, e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCl in dioxane, boron tris-(trifluoroacetate) and cyanogen bromide, and reaction in solution with isolation and purification of intermediates is well-known classical peptide methodology.

The preferred peptide synthesis method follows conventional Merrifield solid-phase procedures. See Merrifield, *J. Amer. Chem. Soc.* 85, 2149–54 (1963) and *Science* 150, 178–85 (1965). This procedure, though using many of the same chemical reactions and blocking groups of classical peptide synthesis, provides a growing peptide chain anchored by its carboxy terminus to a solid support, usually cross-linked polystyrene, styrenedivinylbenzene copolymer or, preferably, p-methylbenzhydrylamine polymer for synthesizing peptide amides. This method conveniently simplifies the number of procedural manipulations since removal of the excess reagents at each step is effected simply by washing the polymer.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in *Advances in Enzymology* 32, pp. 221–296, F. F. Nold, Ed., Interscience Publishers, New York, 1969; and Erickson and Merrifield, *The Proteins*, Vol. 2, p. 255 et seq. (ed. Neurath and Hill), Academic Press, New York, 1976.

In order to illustrate the invention in further detail, the following specific laboratory examples were carried out. Although specific examples are thus illustrated herein, it will be appreciated that the invention is not limited to these specific examples.

The HepG2 cell line described herein is a well-known and widely available human hepatoma cell line whose establishment and characteristics are described in U.S. Pat. No. 4,393,133. Samples of this cell line also are available to the public from the permanent collection of the American Type Culture Collection, Rockville, Md., under accession number ATCC HB 8065.

EXAMPLE

Materials. Peptides were synthesized by conventional solid phase synthesis procedures as described above, purified and subjected to amino acid composition and fast atom bombardment mass spectrometry (FAB-MS). Purified human plasma $\alpha_1$ AT and leukocyte elastase were prepared by conventional procedures as previously described by Perlmutter et al., *J. Clin. Invest.* 81, 1744–1780 (1988). TpCK-treated bovine pancreatic trypsin was purchased from Sigma Chemical Company, St. Louis, Mo. Proteinase K was purchased from Boehringer Mannheim Corp. (BMC).

Competitive Binding and Internalization Assays.

Confluent monolayers of HepG2 cells and human blood monocytes from normal individuals were established in 24-well tissue culture plates by conventional procedures as previously described by C. Barbey-Morel et al., *J. Exp. Med.* 166, 1041–1054 (1987). Peptide 105Y, peptide 105C and trypsin were labeled with $^{125}$I using chloramine T. Peptide 105Y was purified by gel filtration on BioGel P2 (Bio-Rad), peptide 105C by reverse phase C-18 chromatography and trypsin by gel filtration on Sephadex G-10. For complexes, $^{125}$I trypsin or unlabelled trypsin was incubated for 20 mins at 37° C. with unlabelled $\alpha_1$ AT in equimolar concentrations. The reaction was terminated by the addition of phenylmethylsulfonyl fluoride (PMSF) to a final concentration of 2mM. These conditions were shown to be optimal for formation of the 66- and 75 kD forms of the trypsin-$\alpha_1$ AT complex by their presence on Coomassie blue-stained SDS-polyacrylamide gels for unlabelled complexes and on autoradiograms of SDS-polyacrylamide gels for labelled complexes. For binding studies, HepG2 cells were washed with phosphate-buffered saline (PBS) containing 1 mM CaCl$_2$ and 1 mM MgCl$_2$ and incubated at 4° C. for 2 hrs with $^{125}$I-ligand and unlabelled candidate competitors diluted in binding medium (Dulbecco's modified Eagle's medium containing 10 mM Hepes, 0.1 mg/ml cytochrome c, 0.01% Tween 80 [Polysorbate 80], 1 mg/ml bovine serum albumin). The cells were then rinsed in PBS and cell-associated radioactivity determined in 1 N NaOH homogenates. For internalization studies, HepG2 cells were washed with PBS and then incubated at 37° C. for 1 hour with $^{125}$I ligand and unlabelled candidate competitors diluted in binding medium. The cells were then rinsed and incubated for an additional 1 hour at 4° C. in PBS with Proteinase K (0.5 mg/ml) to strip away any surface-bound $^{125}$I ligand The effect of Proteinase K was terminated by the addition of 1 mM PMSF. Cells were then detached by gentle agitation and pelleted by centrifugation. Radioactivity in these cell pellets represented internalized $^{125}$I ligand. Some of the peptides used as candidate competitors, especially the pentapeptides, were dissolved in dimethylsulfoxide (DMSO) because they were not soluble in water. For all of these tests the same final concentration of DMSO was added to each cell monolayer. For peptides which were soluble in both water and DMSO (peptides 105Y, 105B, 105C, 154) there were no differences in binding characteristics as a result of these solvents.

Metabolic labeling. Confluent monolayers were rinsed and incubated at 37° C. in the presence of methionine-free medium containing [$^{35}$S]methionine at 250 uCi/ml. To determine the net synthesis of $\alpha_1$ AT and a control protein, factor B [Perlmutter, *Pharm. Therap.* 34, 247 (1987)], cells were subjected to a short pulse (20 min) and radiolabeled $\alpha_1$ 1 AT or factor B was assayed in the cell lysates. Solubilization of cells, clarification of cell lysates after labeling, assay of total protein synthesis, immunoprecipitation, and SDS-PAGE were carried out by conventional procedures as previously described by C. Barbey-Morel, *J. Exp. Med.* 166, 1041–1054 (1987); Roberts and Paterson, *Proc. Natl. Acad. Sci. USA* 70, 2330–2334 (1973); Laemmli, *Nature* 27, 680–685 (1980).

RESULTS

Evidence that Pentapeptide 370–374 of $\alpha_1$ AT is Recognized by the SEC Receptor.

Figure 1A:
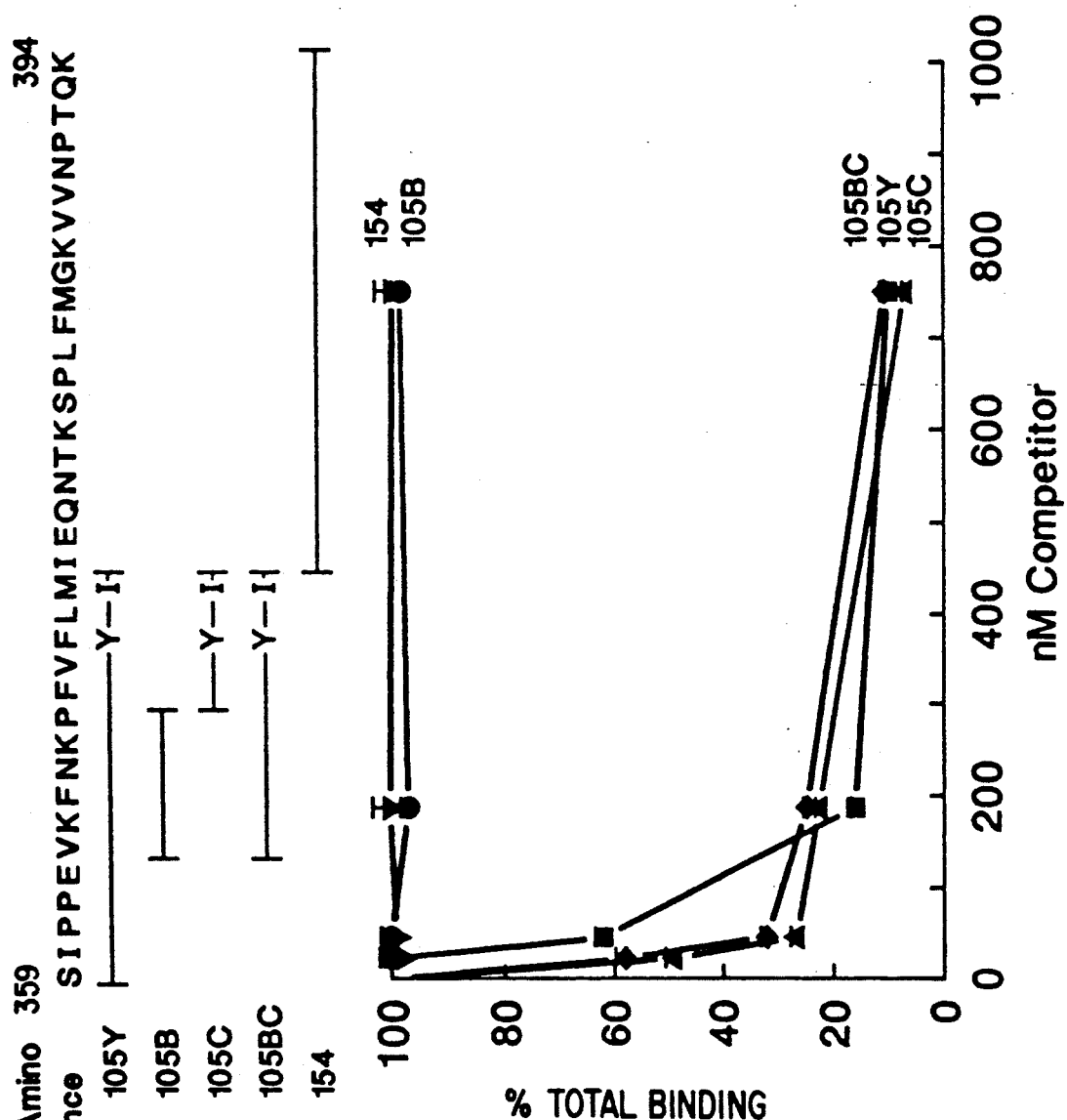

Previous tests have localized the receptor-binding domain of $\alpha_1$ AT-elastase complexes to amino acids 359–374 of $\alpha_1$ AT. In order to determine the minimal requirements for binding of $\alpha_1$ AT-elastase complexes, synthetic peptides based on the sequence of amino acids 363–369 (peptide 105B), 370–374 (peptide 105C) and 363–374 (peptide 105BC) were examined as competitors for binding of $^{125}$I peptide 105Y (359–374) to HepG2 cells (FIG. 1a). In each of these peptides there is an F to Y substitution at residue 372 to allow for subsequent radioiodination and an M to I substitution at 374 for ease of synthesis. The results indicate surprisingly that peptide 105C and peptide 105BC compete as effectively as peptide 105Y but that peptide 105B does not compete at all for cell surface binding. A negative control, peptide 154, which corresponds to the sequence of $\alpha_1$ AT from amino acids 375–394, does not compete for binding. The pentapeptide FVYLI, based on $\alpha_1$ AT sequence 370–374, could therefore completely account for binding previously attributed to $\alpha_1$ AT 359–374.

Figure 1B:
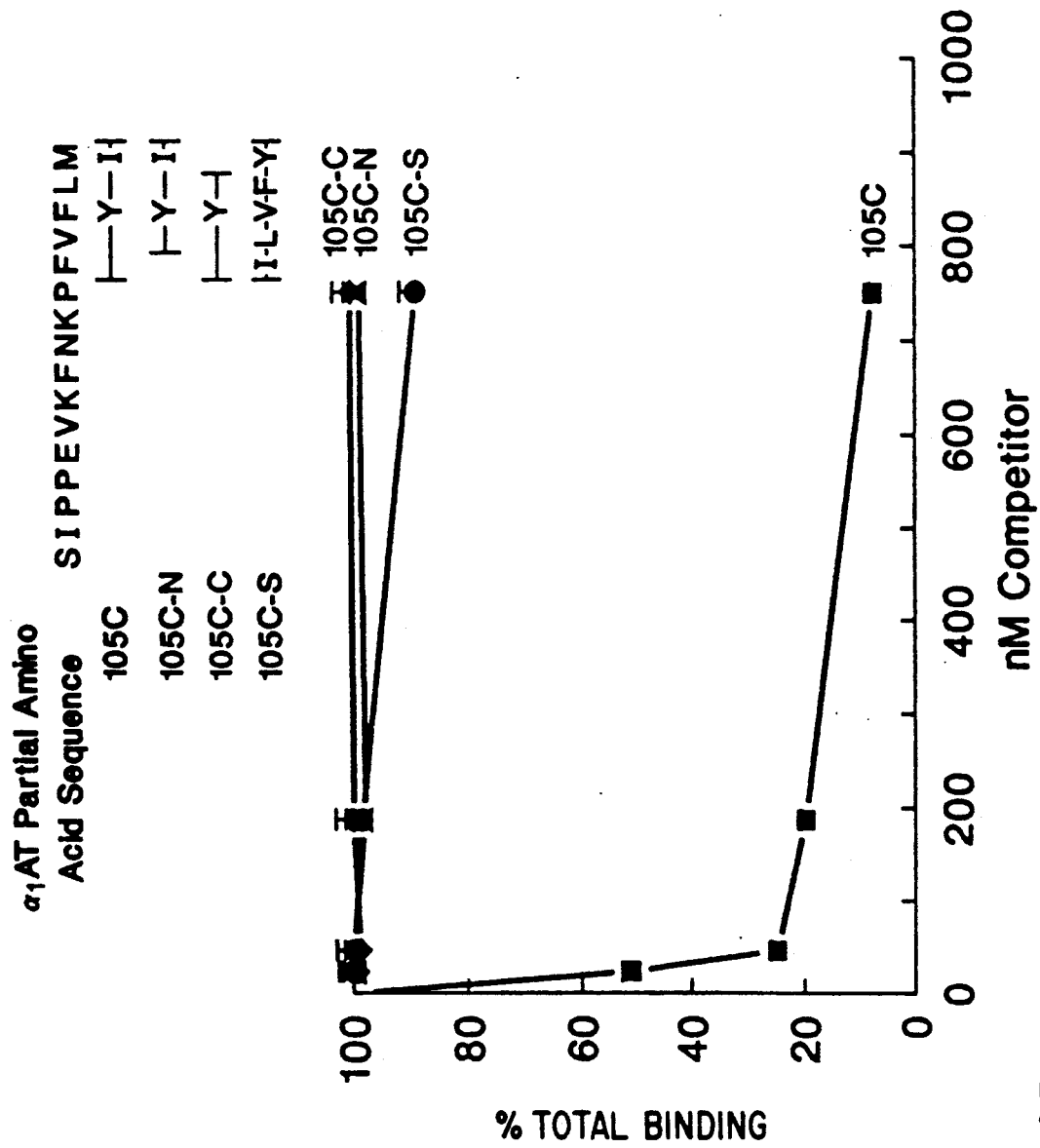
Figure 1C:
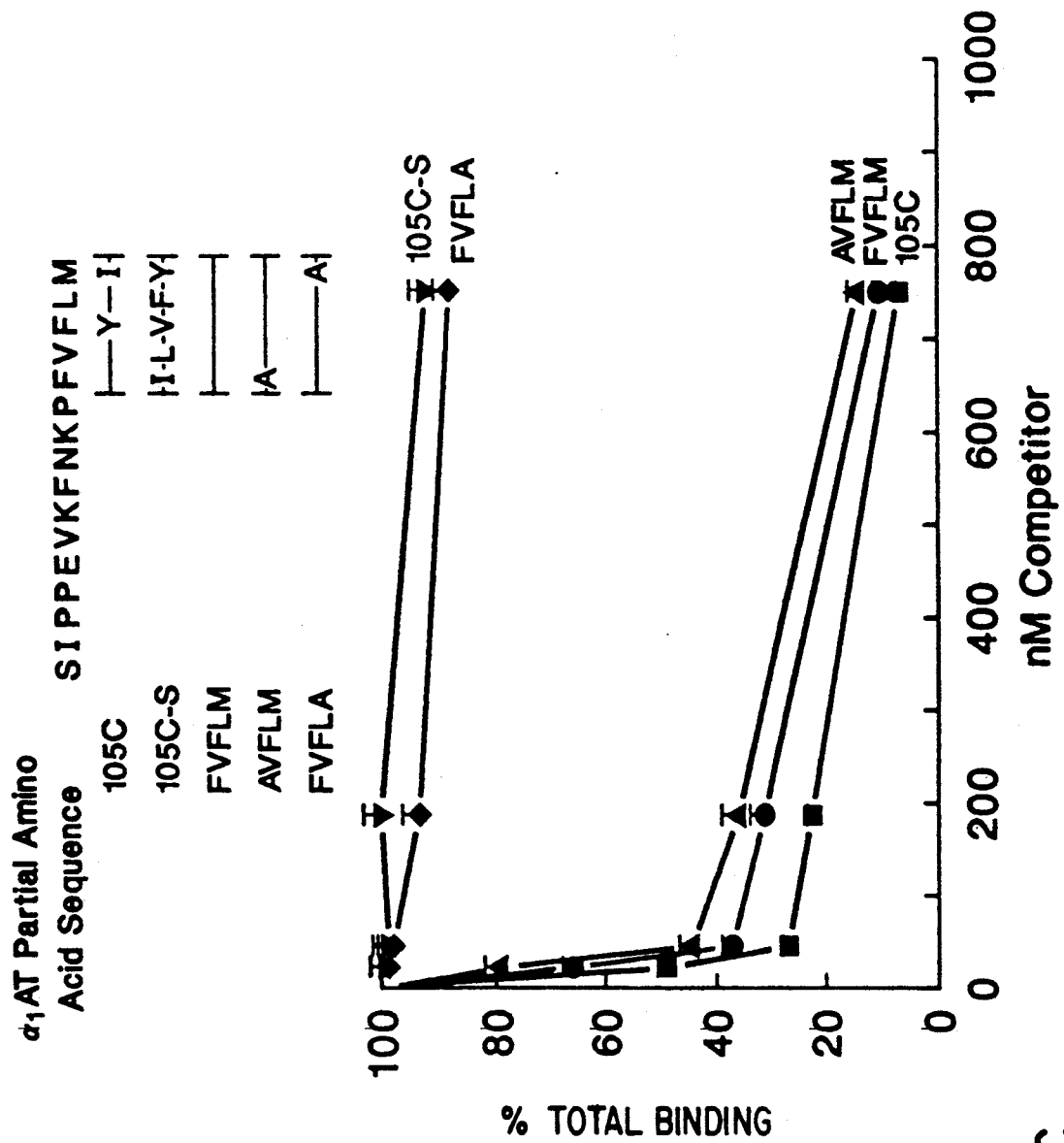

In order to determine whether binding of this pentapeptide to HepG2 cells was sequence-specific, synthetic peptides in which specific amino acids were deleted (peptide 105C-N, Peptide 105C-C) or in which the sequence was scrambled (peptide 105C-S) were examined as competitors for binding of $^{125}$I peptide 105Y (FIG. 1b). The results demonstrate surprisingly that deletion of the amino-terminal F$_{370}$ or the carboxy terminal I$_{374}$ or scrambling of the sequence completely abrogates competitive binding of this pentapeptide.

Finally, the effect of specific amino acid substitutions on competitive binding of the pentapeptide 105C (FIG. 1c) Was examined. In this series of tests it was first shown that there was no significant difference in the competitive binding of peptide FVFLM which is identical to $\alpha_1$ AT sequence 370–374, and peptide 105C (FVYLI). It was then shown that an F to A substitution at residue 370 only minimally affects the competitive binding efficacy of pentapeptide FVFLM but an M to A substitution at residue 374 completely abrogates binding. Taken together these data indicate that binding of $\alpha_1$ AT pentapeptide FVFLM to HepG2 cells is sequence-specific in that it is altered by substitutions, deletions and scrambling of the sequence.

Figure 2A:
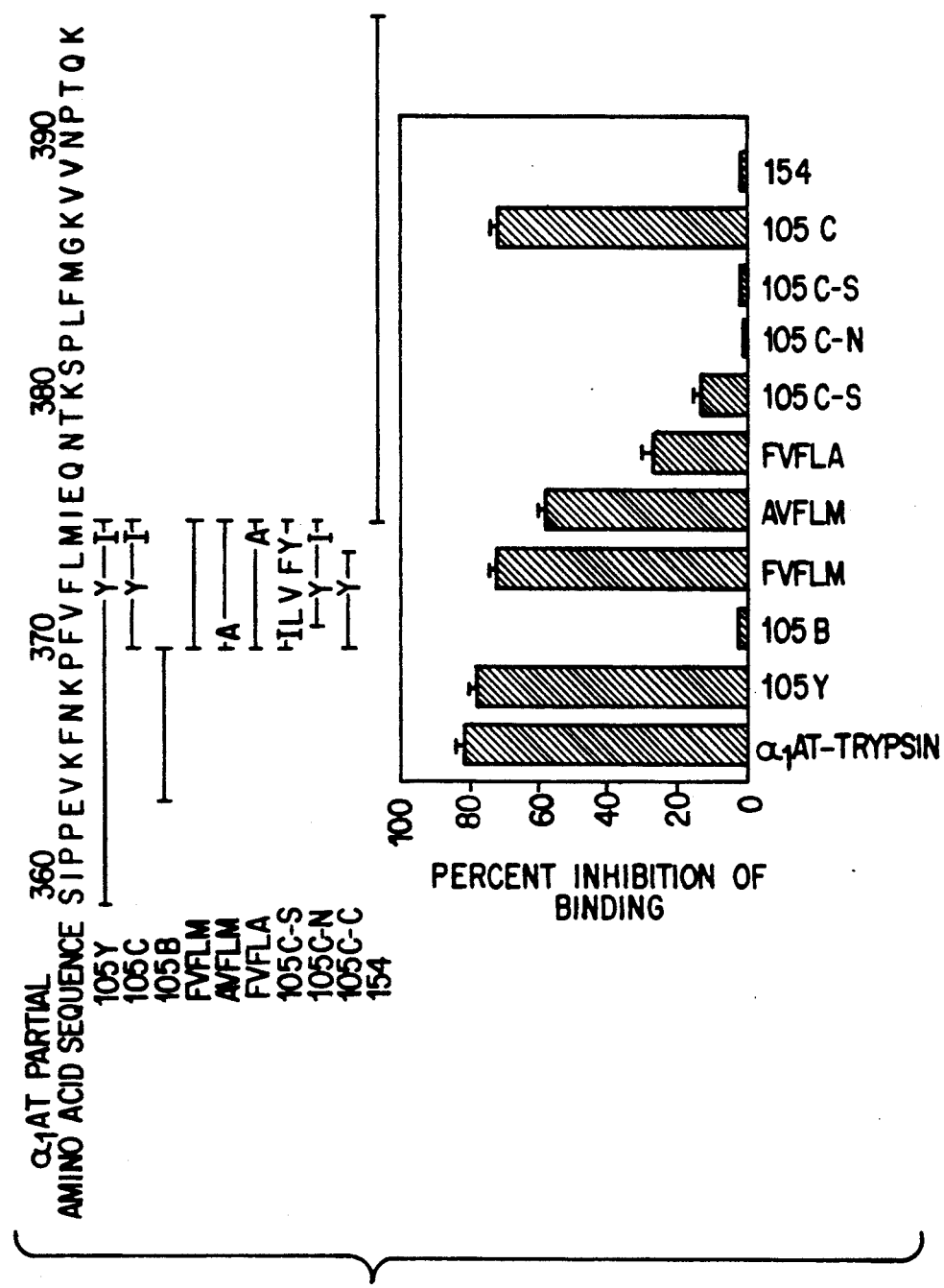

It was then investigated whether pentapeptide FVFLM inhibits binding of $\alpha_1$ AT-protease complexes (FIG. 2a). For these tests, $\alpha_1$ AT-$^{125}$I trypsin complexes were used as labelled ligand since previous work had shown that these had relatively higher specific radioactivity but binding characteristics that were identical to those of $^{125}$I$\alpha_1$ AT-trypsin and $^{125}$I$\alpha_1$ AT-neutrophil elastase complexes. The results indicate that pentapeptide FVFLM inhibits binding of $\alpha_1$ AT-$^{125}$I trypsin complexes to HepG2 cells as effectively as unlabelled $\alpha_1$ AT-trypsin complexes, peptide 105Y and peptide 105C. Binding of $\alpha_1$ AT-$^{125}$I trypsin complexes was not inhibited by negative control peptides 105B and 154, by deleted peptides 105C-N and 105C-C or by scrambled peptide 105C-S. Substitution of A for F at residue 370 reduces competitive binding modestly but substitution of A for M at residue 374 almost completely abrogates competitive binding.

Figure 2B:
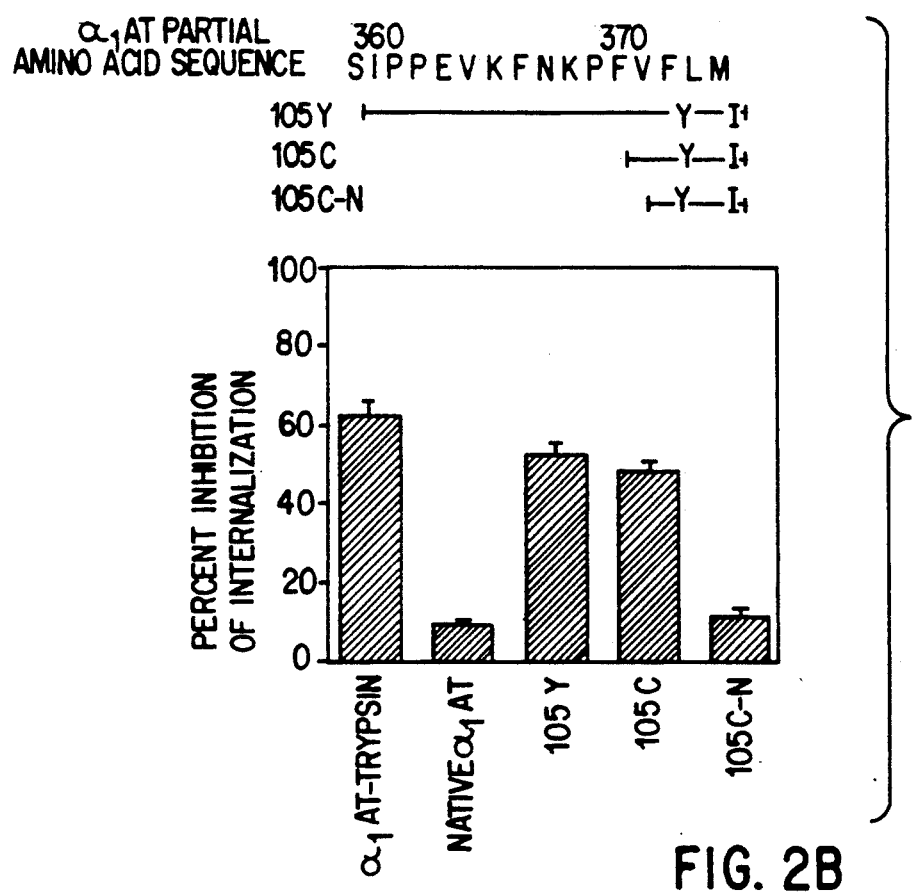

In order to determine whether receptor-mediated internalization of $\alpha_1$ AT-protease complexes by HepG2 cells is also inhibited by the pentapeptide region of $\alpha_1$ AT from residues 370-374, cells were incubated for 60 minutes at 37° C. with $^{125}$I-trypsin complexes in the absence or presence of putative competitors in 50-fold molar excess (FIG. 2b). The cells were then rinsed extensively and incubated with Proteinase K for an additional 60 minutes at 4° C. to remove any surface bound radiolabelled ligand. Internalization was defined as radioactivity associated with the resulting cell pellet. The results demonstrate that pentapeptide 105C inhibits internalization as effectively as peptide 105Y and unlabelled $\alpha_1$ AT-trypsin complexes. Higher degrees of inhibition were achieved by higher concentrations of competitors in other tests. There was no significant inhibition of internalization by a deleted peptide (105C-N) or by native $\alpha_1$ AT.

The direct binding of peptide 105C to HepG2 cells was also examined. This peptide was radioiodinated by the chloramine T method and purified by reverse phase C:18 chromatography. Separate monolayers of cells were incubated with $^{125}$I-105C in several different concentrations either in the absence or presence of unlabelled 105C in 200-fold molar excess (FIG. 3, left panel a). There is specific and saturable binding with the point of half-maximal saturation, ~40nM, almost identical to that for $\alpha_1$ AT-$^{125}$I trypsin complexes and to that predicted by Scatchard analysis of $^{125}$I 105Y binding. In separate tests binding of $^{125}$I 105C was inhibited by unlabelled 105Y and unlabelled $\alpha_1$ AT-trypsin complexes (FIG. 3, right panel b) but not by unlabelled native $\alpha_1$ AT.

Effect of Pentapeptide 370-374 of $\alpha_1$ AT on Synthesis of $\alpha_1$ AT.

Synthetic peptides as short as 14 amino acids in length, and containing sequences corresponding to $\alpha_1$ AT 370-374, are capable of mediating increases in synthesis of $\alpha_1$ AT in human monocytes and HepG2 cells. The synthetic peptides generated during these tests were examined for their effect on synthesis of $\alpha_1$ AT (FIG. 4). Separate monolayers of monocytes cells were incubated for 5 hours at 37° C. in serum-free control medium or medium supplemented with peptides in several different concentrations. Medium was supplemented with polymyxin B at concentrations which completely abrogate the effect of endotoxin on synthesis of $\alpha_1$ AT. The monolayers were then rinsed vigorously and subjected to metabolic labelling with $^{35}$S methionine. The results demonstrate that peptide 105BC, 12 amino acids in length, mediates a concentration-dependent increase in synthesis of $\alpha_1$ AT but peptide 105B which contains 7 of these residues has no effect (left panel a). The effect of peptide 105BC on synthesis of $\alpha_1$ AT is specific in that it does not affect total protein synthesis or synthesis of another secretory protein, complement protein factor B (right panel b). Peptide 105BC also mediated an increase in synthesis of $\alpha_1$ AT in HepG2 cells.

Further Characteristics of the Receptor-Binding Domain of $\alpha_1$ AT.

In another series of tests, the effect of alanine substitution at each of the residues within the pentapeptide FVFLM on competition for binding of $^{125}$I trypsin-$\alpha_1$ AT complexes to HepG2 cells (FIG. 5) was examined. Substitution of A for F$_{37}$ (peptide AVFLM) only minimally affected competitive binding efficacy. Similar results were obtained with this particular peptide in previous tests (FIG. 2a). Substitution of A for V$_{371}$ (peptide FAFLM) had no effect and substitution of A for F$_{372}$ (peptide FVALM) caused an approximately 10% increase in competitive binding efficacy. Substitution of A for L$_{373}$ (peptide FVFAM) and A for M$_{374}$ (peptide FVFLA) reduced competitive binding efficacy by 18% and 56%, respectively. These results provide further evidence for the unique sequence-specificity of recognition by the SEC receptor. Substitution of the neutral amino acid alanine at residues 370, 371 and 372 only minimally affects binding but substitution of alanine at residues 373 and 374 abrogates recognition to a moderate and severe extent, respectively.

Alignment of the sequence of $\alpha_1$ AT with other serpin family members shows that the receptor binding pentapeptide at residues 370-374 of $\alpha_1$ AT is highly conserved in the sequence of these other members (see FIG. 7 below). There is also a high degree of similarity in the sequence corresponding to amino acids KP 368-369 of $\alpha_1$ AT. Two approaches were used to address the possibility that KP 368-369 contributes to the receptor binding recognition sequence. First, peptides FVFLM and FVYLI (also called peptide 105C) were compared to peptide KPFVFLM as competitors for binding of $^{125}$I peptide 105Y to HepG2 cells (FIG. 6). Even at relatively low concentrations (10- to 30-fold molar excess), there was no difference in inhibition of binding by these two peptides. Second, peptide FVYL was compared to peptide KPFVFL as competitors for binding of $^{125}$I peptide 105Y to HepG2 cells. Peptide FVYL was one of the original deleted peptides (peptide 105C-C in FIG. 1b and 2a), being based on peptide 105C but having the carboxy terminal residue 374 deleted. This peptide does not compete at all for binding of $^{125}$I peptide 105Y (FIG. 1b) or for binding of $^{125}$I trypsino-$\alpha_1$ AT complexes (FIG. 2a) to HepG2 cells. It was reasoned that if KP 368-369 of the $\alpha_1$ AT sequence contributed to the receptor recognition sequence it would be apparent in the competitive binding efficacy of a peptide in which KP was added to the amino terminus of a peptide like FVYL. The results indicate that peptide KPFVFL has only a minimal inhibitory effect on the binding of $^{125}$I peptide 105Y. At 30-fold molar excess it inhibits binding of $^{125}$I peptide 105Y by only 17.8±1.3%. These results indicate that if KP contributes to the receptor binding recognition sequence it does so to a minimal extent.

Additional studies confirm that substance P, bombesin and amyloid-β-protein compete for binding to, and cross-linking of, the SEC receptor of HepG2 cells. The SEC receptor is distinct from the substance P receptor described by Hershey and Krause, *Science* 246, 958–962 (1990): there is no substance P receptor mRNA in HepG2 cells; the SEC receptor is present in much higher density on the plasma membrane of receptor-bearing cells and binds its ligands at lower affinity than the substance P receptor; the SEC receptor is much less restricted in the specificity with which it recognizes ligand; and ligands for the SEC receptor including peptide 105Y, $\alpha_1$ AT-protease complexes, bombesin and amyloid-β-protein do not compete for binding of substance P to a stable transfected cell line expressing the substance P receptor. It is, therefore, believed that biological activities previously ascribed to the substance P receptor, including the recently described neurotrophic and neurotoxic effects of the amyloid-β-protein by Yankner et al, *Science* 250, 279–282 (1990), may actually be medicated by the SEC receptor. Amyloid-β-protein is known to be present in neuritic plaques and cerebrovascular deposits in individuals with Alzheimer's disease and Down's syndrome. This suggests a further potential use of the novel binding peptides of the present invention. Recombinant amyloid-β-related protein and protease inhibitors and their application to Alzheimer's disease diagnosis and therapy is disclosed, e.g., in PCT WO 90/14840 and 90/18441, published Dec. 13, 1990.

Amino acids are shown herein either by standard one letter or three letter abbreviations as follows:

| Abbreviated | Designation | Amino Acid |
| --- | --- | --- |
| A | Ala | Alanine |
| C | Cys | Cysteine |
| D | Asp | Asparatic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Various other examples will be apparent to the person skilled in the art after reading the present disclosure without departing from the spirit and scope of the invention. It is intended that all such other examples be included within the scope of the appended claims.

( 1 ) GENERAL INFORMATION:

( i i i ) NUMBER OF SEQUENCES: 26

( v i ) CURRENT APPLICATION DATA:
           ( A ) APPLICATION NUMBER: 07/690,284
           ( B ) FILING DATE: 24-APR-1991

( 2 ) INFORMATION FOR SEQ ID NO:1:

( i ) SEQUENCE CHARACTERISTICS:
           ( A ) LENGTH: 16 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:1:

Ser Ile Pro Pro Glu Val Lys Phe Asn Lys Pro Phe Val Tyr Leu Ile
1               5                   10                  15

( 2 ) INFORMATION FOR SEQ ID NO:2:

( i ) SEQUENCE CHARACTERISTICS:
           ( A ) LENGTH: 5 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:2:

Phe Val Phe Leu Met (2) INFORMATION FOR SEQ ID NO:3:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:3:

Phe Val Tyr Leu Ile
1               5

(2) INFORMATION FOR SEQ ID NO:4:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:4:

Ala Val Phe Leu Met
1               5

(2) INFORMATION FOR SEQ ID NO:5:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

Phe Val Phe Leu Ala
1               5

(2) INFORMATION FOR SEQ ID NO:6:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:6:

Phe Val Ala Leu Met
1               5

(2) INFORMATION FOR SEQ ID NO:7:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide ( x i ) SEQUENCE DESCRIPTION: SEQ ID NO:7:

Phe Val Tyr Leu
1

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Glu Val Lys Phe Asn Lys Pro
1               5

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Lys Pro Phe Val Phe Leu
1               5

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Phe Ala Phe Leu Met
1               5

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Phe Val Phe Ala Met
1               5

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Lys Pro Phe Val Phe Leu Met
1                         5

( 2 ) INFORMATION FOR SEQ ID NO:13:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Ser Ile Pro Pro Glu Val Lys Phe Asn Lys Pro Phe Val Phe Leu Met
1               5                   10                  15

Ile Glu Gln Asn Thr Lys Ser Pro Leu Phe Met Gly Lys Val Val Asn
            20                  25                  30

Pro Thr Gln Lys
            35

( 2 ) INFORMATION FOR SEQ ID NO:14:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Ser Ile Pro Pro Glu Val Lys Phe Asn Lys Pro Phe Val Phe Leu Met
1               5                   10                  15

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Phe Leu Val Phe Ile
1               5

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
       Phe Leu Met Ile Ile
       1               5
```

(2) INFORMATION FOR SEQ ID NO:17:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
       Phe Leu Phe Val Leu
       1               5
```

(2) INFORMATION FOR SEQ ID NO:18:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
       Phe Leu Phe Leu Ile
       1               5
```

(2) INFORMATION FOR SEQ ID NO:19:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
       Phe Leu Phe Val Val
       1               5
```

(2) INFORMATION FOR SEQ ID NO:20:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
       Phe Leu Phe Leu Ile
       1               5
```

(2) INFORMATION FOR SEQ ID NO:21:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide ( x i ) SEQUENCE DESCRIPTION: SEQ ID NO:21:

Phe Leu Phe Phe Ile
1                   5

( 2 ) INFORMATION FOR SEQ ID NO:22:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

Phe Leu Met Phe Ile
1                   5

( 2 ) INFORMATION FOR SEQ ID NO:23:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

Phe Met Leu Leu Ile
1                   5

( 2 ) INFORMATION FOR SEQ ID NO:24:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

Phe Ile Ile Met Ile
1                   5

( 2 ) INFORMATION FOR SEQ ID NO:25:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

Phe Leu Phe Cys Ile
1                   5

( 2 ) INFORMATION FOR SEQ ID NO:26:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:26:

Phe Leu Phe Ala Val
1              5

What is claimed is:

1. A novel peptide that binds to the SEC receptor selected from the group consisting of pentapeptides having the following sequences:

2. The peptide of claim 1 having the sequence Phe-Val-Phe-Leu-Met [SEQ ID NO:2].

3. The peptide of claim 1 having the sequence Phe-Val-Tyr-Leu-Ile [SEQ ID NO:3].

4. The peptide of claim 1 having the sequence Ala-Val-Phe-Leu-Met [SEQ ID NO:4].

5. The peptide of claim 1 having the sequence Phe-Val-Phe-Leu-Ala [SEQ ID NO:5]

6. The peptide of claim 1 having the sequence Phe-Val-Ala-Leu-Met [SEQ ID NO:6].

* * * * *

UNITED STATES PATENT AND TRADEMARK OFFICE
CERTIFICATE OF CORRECTION

PATENT NO. : 5,175,253
DATED : DEC. 29, 1992
INVENTOR(S) : ROBERT J. FALLON, et al

It is certified that error appears in the above-identified patent and that said Letters Patent is hereby corrected as shown below:

At col. 8, line 22, "$F_{37}$" should read --$F_{370}$--

At col. 21, in line 3 of Claim 1, after "sequences:" insert

--Phe-Val-Phe-Leu-Met [SEQ ID NO:2],
Phe-Val-Tyr-Leu-Ile [SEQ ID NO:3],
Ala-Val-Phe-Leu-Met [SEQ ID NO:4],
Phe-Val-Phe-Leu-Ala [SEQ ID NO:5] and
Phe-Val-Ala-Leu-Met [SEQ ID NO:6] ---.

Signed and Sealed this

Twenty-sixth Day of September, 1995

Attest:

BRUCE LEHMAN

Attesting Officer

Commissioner of Patents and Trademarks